(12) United States Patent
Chen et al.

(10) Patent No.: US 10,769,781 B2
(45) Date of Patent: Sep. 8, 2020

(54) SYSTEM AND METHOD FOR CLOUD MEDICAL IMAGE ANALYSIS USING SELF-LEARNING MODEL

(71) Applicant: TAIHAO MEDICAL INC., Taipei (TW)

(72) Inventors: Rong-Tai Chen, Taichung (TW); Hong-Hao Chen, Hsinchu (TW); Jen-Feng Hsu, Taoyuan (TW); Ruey-Feng Chang, Taichung (TW); Hsin-Hung Lai, Taipei (TW); Yuan-Yen Chang, Taichung (TW)

(73) Assignee: TAIHAO MEDICAL INC., Taipei (TW)

( * ) Notice: Subject to any disclaimer, the term of this patent is extended or adjusted under 35 U.S.C. 154(b) by 257 days.

(21) Appl. No.: 15/948,983

(22) Filed: Apr. 9, 2018

(65) Prior Publication Data

US 2018/0308234 A1 Oct. 25, 2018

(30) Foreign Application Priority Data

Apr. 24, 2017 (TW) .............................. 106113572 A

(51) Int. Cl.
*G16H 50/30* (2018.01)
*G16H 30/20* (2018.01)
(Continued)

(52) U.S. Cl.
CPC ............. *G06T 7/0012* (2013.01); *G06N 3/08* (2013.01); *G16H 30/20* (2018.01); *G16H 30/40* (2018.01);
(Continued)

(58) Field of Classification Search
None
See application file for complete search history.

(56) References Cited

U.S. PATENT DOCUMENTS 5,982,917 A * 11/1999 Clarke ................. G06T 7/0012
128/922
6,125,194 A 9/2000 Yeh et al.
(Continued)

FOREIGN PATENT DOCUMENTS

CN 106355023 1/2017
JP 2003150714 5/2003
(Continued)

OTHER PUBLICATIONS

"Office Action of Japan Counterpart Application," dated Sep. 17, 2019, p. 1-p. 4.
(Continued)

*Primary Examiner* — Idowu O Osifade
(74) *Attorney, Agent, or Firm* — JCIPRNET

(57) ABSTRACT

A system and a method for cloud medical image analysis are provided. The system for cloud medical image analysis has a cloud medical analysis platform and an electronic device. The electronic device obtains a medical image. The electronic device quantifies the medical image to obtain a first feature value. The electronic device sends the first feature value to the cloud medical analysis platform. The cloud medical analysis platform inputs the first feature value into an analysis module to obtain an analysis result, wherein the analysis module uses a self-learning module and the analysis module is trained via a plurality of training images. The cloud medical analysis platform sends the analysis result to the electronic device.

16 Claims, 2 Drawing Sheets

(51) Int. Cl.
    *G16H 30/40*     (2018.01)
    *G06T 7/00*     (2017.01)
    *G06N 3/08*     (2006.01)

(52) U.S. Cl.
    CPC ... *G16H 50/30* (2018.01); *G06T 2207/20081* (2013.01); *G06T 2207/30096* (2013.01)

(56) References Cited

U.S. PATENT DOCUMENTS

| | | |
|---|---|---|
| 7,640,051 B2 | 12/2009 | Krishnan et al. |
| 9,324,022 B2 | 4/2016 | Williams, Jr. et al. |
| 9,589,374 B1 | 3/2017 | Gao et al. |
| 2004/0147840 A1 | 7/2004 | Duggirala et al. |

FOREIGN PATENT DOCUMENTS

| | | |
|---|---|---|
| JP | 2009512528 | 3/2009 |
| JP | 2009514583 | 4/2009 |
| JP | 2014113364 | 6/2014 |
| JP | 2015510157 | 4/2015 |
| JP | 2017068380 | 4/2017 |
| JP | WO2015166692 | 4/2017 |
| TW | M535807 | 1/2017 |
| WO | 2017023569 | 2/2017 |

OTHER PUBLICATIONS

"Search Report of Europe Counterpart Application", dated Sep. 25, 2018, p. 1-p. 10.

Clay Spence, et al., "Applications of multi-resolution neural networks to mammography," Jan. 1, 1999, XP55507227, retrieved form the Internet: Available at: https://papers.nips.cc/paper/1506-applications-of-multi-resolution-neural-networks-to-mammography.pdf (retrieved on Sep. 14, 2018).

"Office Action of Japan Counterpart Application," dated Mar. 26, 2019, p. 1-p. 3.

* cited by examiner

SYSTEM AND METHOD FOR CLOUD MEDICAL IMAGE ANALYSIS USING SELF-LEARNING MODEL

CROSS-REFERENCE TO RELATED APPLICATION

This application claims the priority benefit of Taiwan application serial no. 106113572, filed on Apr. 24, 2017. The entirety of the above-mentioned patent application is hereby incorporated by reference herein and made a part of this specification.

BACKGROUND OF THE INVENTION

Field of the Invention

The invention relates to a system and a method for cloud medical image analysis.

Description of Related Art

In general, in the medical field, a computer-aided detection (CADe) module is generally used to detect suspicious lesions, or the properties of the lesions are determined using a computer-aided diagnosis (CADx) module. However, the execution of the CADe module and the CADx module generally requires a greater computational load, and therefore if a diagnostic result is to be obtained using the CADe module and the CADx module, many computing resources and time are generally needed. In terms of execution environment, different CADe or CADx techniques may involve different software and hardware requirements, and the execution of the CADe module and the CADx module needs to meet specified software and hardware requirements.

SUMMARY OF THE INVENTION

The invention provides a system and a method for cloud medical image analysis in which a feature value of a medical image is sent to a cloud medical analysis platform for computation via a cloud computing method to reduce the transmission amount of data and the computing time of a computer-aided detection (CADe) module and a computer-aided diagnosis (CADx) module. The execution environment of the user is not limited to the software and hardware requirements of the CADe and the CADx modules.

The invention provides a system for cloud medical image analysis. The system for cloud medical image analysis has a cloud medical analysis platform and an electronic device. The electronic device obtains a medical image, the electronic device quantifies the medical image to obtain a first feature value, the electronic device sends the first feature value to the cloud medical analysis platform, the cloud medical analysis platform inputs the first feature value to an analysis module to obtain an analysis result, and the cloud medical analysis platform sends the analysis result to the electronic device, wherein the analysis module adopts a self-learning model, the model can be a deep-learning model such as a deep neural network, convolution neural network, deep confidence network, and recursive neural network, and the analysis module is trained via a plurality of training images. The deep-learning model automatically extracts features from the data sufficient to represent data properties via linear or non-linear conversion in a plurality of processing layers, and the input of each continuous processing layer adopts the output of one or a plurality of pre-processing layers. The self-learning is an error correction method, and the self-learning can adopt supervised learning, unsupervised learning, or semi-supervised learning.

The invention provides a method for cloud medical image analysis. The method is used for a system for cloud medical image analysis having a cloud medical analysis platform and an electronic device. The method includes the following: a medical image is obtained via an electronic device; the medical image is quantified via the electronic device to obtain a first feature value; the first feature value is sent to a cloud medical analysis platform via the electronic device; the first feature value is inputted to an analysis module via the cloud medical analysis platform to obtain an analysis result; and the analysis result is sent to the electronic device via the cloud medical analysis platform, wherein the analysis module adopts a self-learning model (such as a deep-learning model) and the analysis module is trained via a plurality of training images.

Based on the above, the system and method for cloud medical image analysis of the invention can generate a feature value according to a medical image via an electronic device, and the cloud medical analysis platform executes the function of a CADe module and/or a CADx module according to the feature value and returns the location of the tumor and/or the diagnostic result of the tumor to the electronic device, and the cloud medical analysis platform can even have a self-learning mechanism based on the feedback from the electronic device to optimize the cloud medical analysis platform. Via this method, the electronic device does not need to actually execute all of the steps of the CADe module and/or the CADx module, and therefore the computational load of the electronic device can be effectively reduced. Moreover, since the electronic device only needs to send the feature value to the cloud medical analysis platform for analysis, the electronic device does not need to send a complete medical image to the cloud medical analysis platform. As a result, the transmission amount of data can be effectively reduced, and the response time of the system can be reduced. In terms of execution environment, the electronic device does not need to be limited to the software and hardware environments of the CADe module and/or the CADx module.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
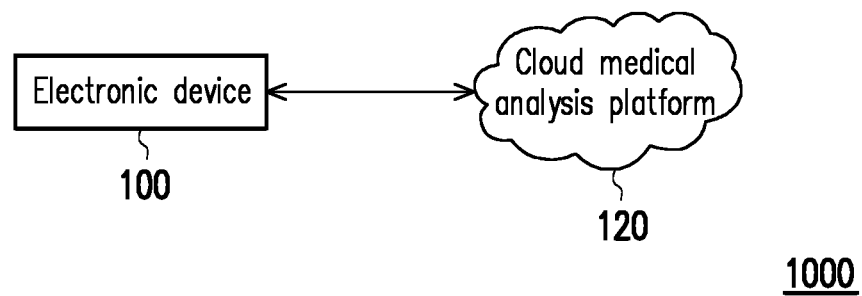
FIG. 1 is a schematic of a system for cloud medical image analysis shown according to an embodiment of the invention.

FIG. 1 is a schematic of a system for cloud medical image analysis shown according to an embodiment of the invention. Referring to FIG. 1, a system 1000 for cloud medical image analysis can include an electronic device 100 and a cloud medical analysis platform 120. The electronic device 100 and the cloud medical analysis platform 120 can communicate via wired or wireless network. It should be mentioned here that, in the invention, the geographical locations of the electronic device 100 and the cloud medical analysis platform 120 are not limited. In other words, the electronic device 100 and the cloud medical analysis platform 120 can be disposed in the same country (or region) for operation. Alternatively, the electronic device 100 and the cloud medical analysis platform 120 can be disposed in different countries (or regions) for operation. For instance, the electronic device 100 can be operated in a first country (such as Taiwan), and the cloud medical analysis platform 120 can be operated in a second country (such as the USA).

Figure 2:
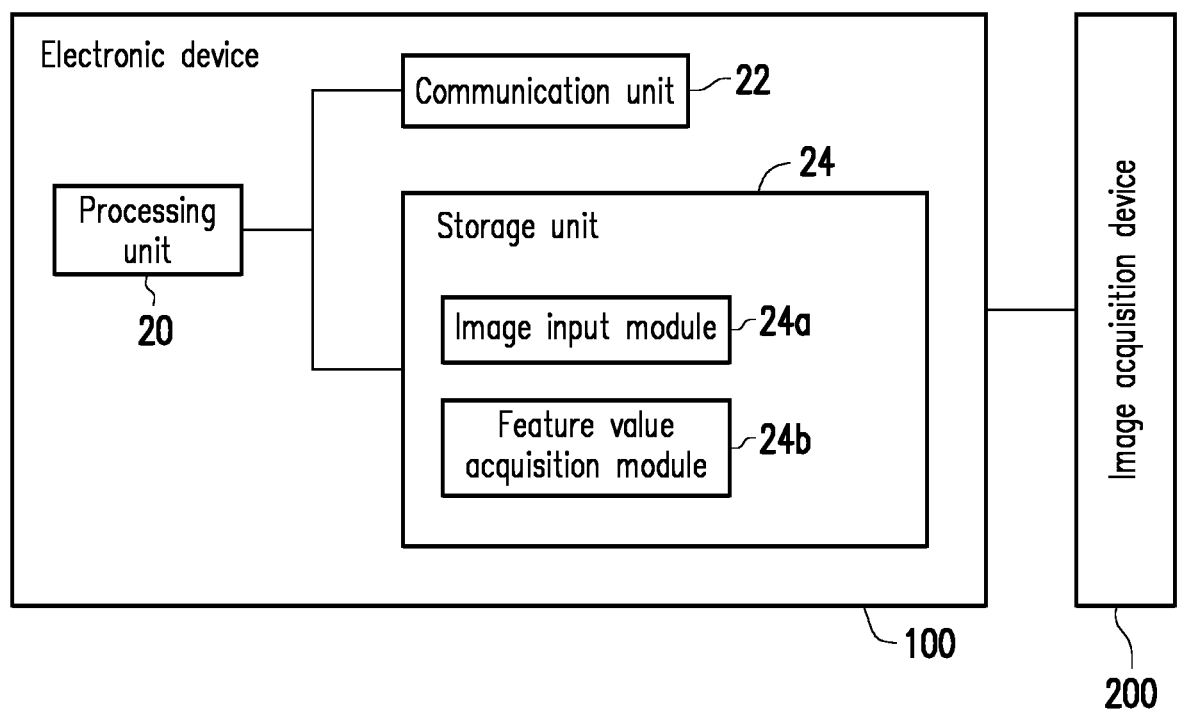
FIG. 2 is a block diagram of an electronic device shown according to an embodiment of the invention.

FIG. 2 is a block diagram of an electronic device shown according to an embodiment of the invention. Referring to FIG. 2, the electronic device 100 includes a processing unit 20, a communication unit 22, and a storage unit 24. In particular, the communication unit 22 and the storage unit 24 are respectively coupled to the processing unit 20. The electronic device 100 is, for instance, an electronic device such as a mobile phone, tablet computer, notebook computer, or robot, and is not limited thereto.

The processing unit 20 can be a central processing unit (CPU) or a programmable microprocessor, digital signal processor (DSP), programmable controller, application-specific integrated circuit (ASIC), or other similar devices or a combination thereof for general use or special use.

The communication unit 22 can be a global system for mobile communication (GSM), personal handy-phone system (PHS), code division multiple access (CDMA) system, wideband code division multiple access (WCDMA) system, long term evolution (LTE) system, worldwide interoperability for microwave access (WiMAX) system, wireless fidelity (Wi-Fi) system, or bluetooth signal transmission device.

The storage unit 24 can be any type of fixed or movable random access memory (RAM), read-only memory (ROM), flash memory, a similar device, or a combination of the devices.

In the present exemplary embodiment, a plurality of code snippets is stored in the storage unit 24 of the electronic device 100, and after the code snippets are installed, the code snippets are executed by the processing unit 20. For instance, the storage unit 24 includes an image input module 24a and a feature value acquisition module 24b, and various operations of the electronic device 100 applied in the system 1000 for cloud medical image analysis are respectively executed via the modules, wherein each module is formed by one or a plurality of code snippets. However, the invention is not limited thereto, and the various operations of the electronic device 100 can also be implemented in other hardware forms.

It should be mentioned here that, the electronic device 100 can be connected to an image acquisition (capture) device 200, and the image acquisition device 200 is, for instance, an ultrasound scanning device, magnetic resonance imaging (MRI), digital breast tomosynthesis (DBT), handheld ultrasound scanner, or automated breast ultrasound system (ABUS) for scanning the patient and obtaining a medical image. However, in another embodiment, the image acquisition device 200 can also be directly integrated in the electronic device 100, the electronic device 100 can be, for instance, directly implemented in the form of an ultrasound scanning device, MRI, DBT, handheld ultrasound scanner, or ABUS, and the electronic device 100 can directly scan the patient to obtain a medical image. In another embodiment, the electronic device 100 can also obtain the medical image via other methods, and in the invention, the acquisition method for obtaining the medical image with the electronic device 100 is not limited.

The image input module 24a in the storage unit 24 is used to obtain at least one segment of medical image. In the present exemplary embodiment, the medical image is a breast image, and the breast image can be a two-dimensional or three-dimensional medical image specifically for the breast area such as automated breast ultrasound (ABUS), digital breast tomosynthesis (DBT), or magnetic resonance imaging (MRI) obtained by the image acquisition device 200. During screening, a three-dimensional image technique can provide more reliable breast density assessment for cancer risk, but the embodiments of the invention are not only limited to a three-dimensional image. In another embodiment, the image input module 24a can also obtain the medical image from the storage unit 24 or via the communication unit 22 (such as Wi-Fi or ethernet), a medical image scanner (such as ABUS scanner or MRI scanner), or a storage device (such as DVD, flash drive, or hard disk).

Figure 3:
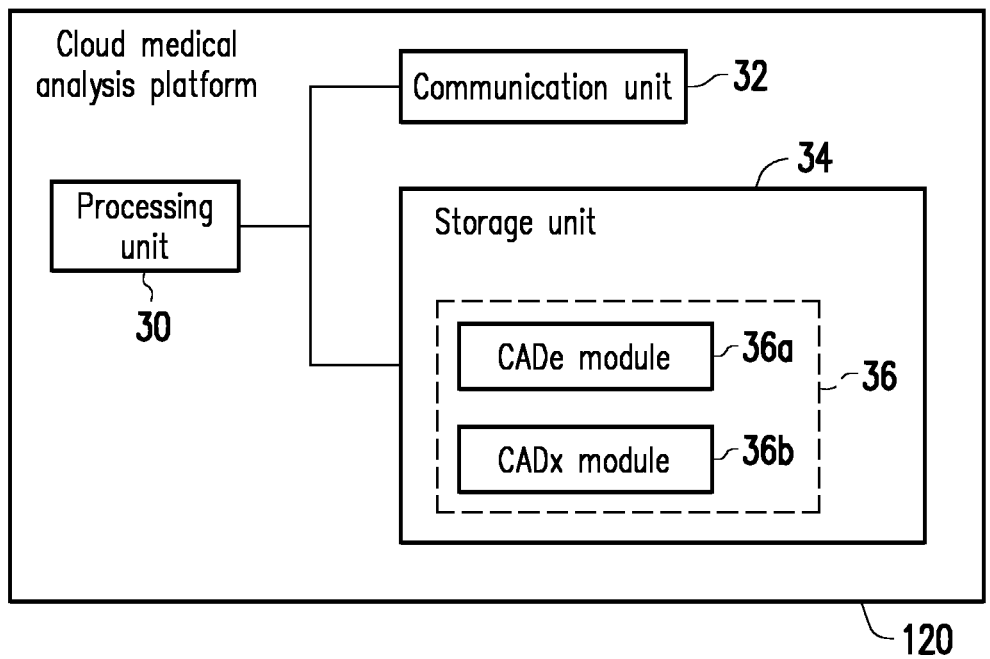
FIG. 3 is a block diagram of a cloud medical analysis platform shown according to an embodiment of the invention.

FIG. 3 is a block diagram of a cloud medical analysis platform shown according to an embodiment of the invention. Referring to FIG. 3, the cloud medical analysis platform 120 of the present embodiment includes a processing unit 30, a communication unit 32, and a storage unit 34. In particular, the communication unit 32 and the storage unit 34 are respectively coupled to the processing unit 30. The processing unit 30, the communication unit 32, and the storage unit 34 can respectively be similar devices to the processing unit 20, the communication unit 22, and the storage unit 24 and are not repeated herein. Moreover, the cloud medical analysis platform 120 is, for instance, a mobile phone, tablet computer, notebook computer, robot, or server, and is not limited thereto. In the present exemplary embodiment, the cloud medical analysis platform 120 can be a server with better computing ability than the electronic device 100.

In the present exemplary embodiment, a plurality of code snippets is stored in the storage unit 34 of the cloud medical analysis platform 120, and after the code snippets are installed, the code snippets are executed by the processing unit 30. For instance, the storage unit 34 includes an analysis module 36 having a CADe module 36a and a CADx module 36b, and the processing unit 30 runs the CADe module 36a and the CADx module 36b in the analysis module 36 to respectively execute various operations of the cloud medical analysis platform 120 applied in the system 1000 for cloud medical image analysis, wherein each module is formed by one or a plurality of code snippets. However, the invention is not limited thereto, and the various operations of the cloud medical analysis platform 120 can also be implemented in other hardware forms.

Figure 4:
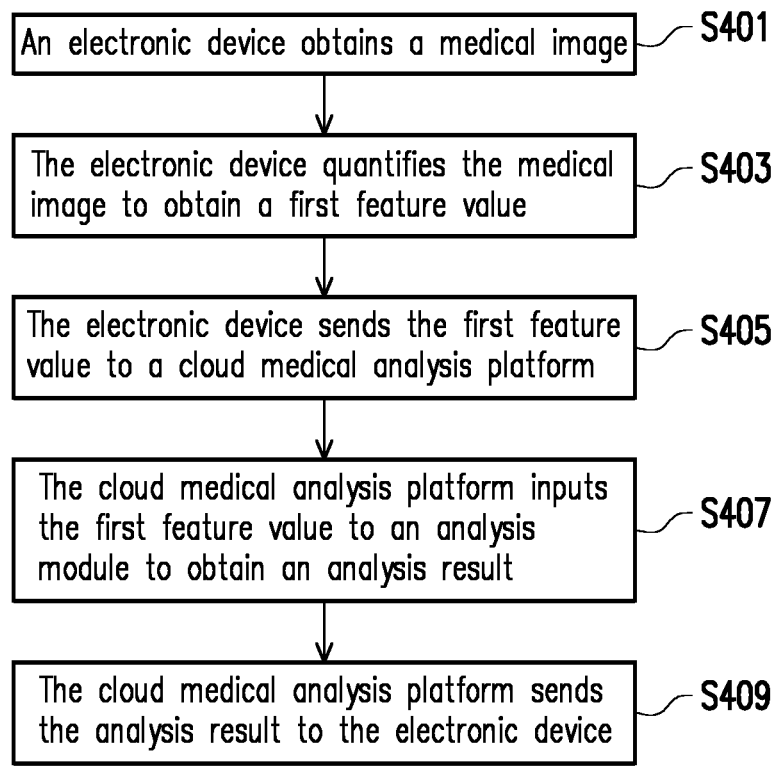
FIG. 4 is a flow chart of a method for cloud medical image analysis shown according to an embodiment of the invention.

FIG. 4 is a flow chart of a method for cloud medical image analysis shown according to an embodiment of the invention.

Referring to all of FIG. 1 to FIG. 4, the method for cloud medical image analysis of FIG. 4 can be applied in the system 100 for cloud medical image analysis in FIG. 1. In step S401, the image input module 24a of the electronic device 100 can obtain a medical image. In the present exemplary embodiment, the medical image is an ultrasound image. However, in other exemplary embodiments, the medical image can also be other types of image based on actual application requirement.

Next, in step S403, the electronic device 100 can quantify the medical image via the feature value acquisition module 24b to obtain a feature value (also referred to as a first feature value).

For instance, after the electronic device 100 obtains the medical image, the feature value acquisition module 24b can, for instance, perform a pre-processing (such as organization clustering or pixel clustering) on the medical image and quantify the features of the medical image after the pre-processing. In particular, the features of the medical image are, for instance, texture, intensity, or shape. However, the invention does not intend to limit the form of the pre-processing and the features in the medical image. In another embodiment, when the CADe module 36a and the CADx module 36b are operated using a region-wise algorithm, the feature value acquisition module 24b can cut the medical image correspondingly using a watershed algorithm to generate a medical image having a plurality of regions, and the feature value acquisition module 24b can quantify the medical image of the regions to generate the corresponding feature value. In another embodiment, when the CADe module 36a and the CADx module 36b are operated using a pixel-wise algorithm, the feature value acquisition module 24b can correspondingly quantify each pixel in the medical image to generate the corresponding feature value.

Next, in step S405, the electronic device 100 sends the first feature value to the cloud medical analysis platform 120. In step S407, the cloud medical analysis platform 120 inputs the first feature value to at least one of the CADe module 36a and the CADx 36b in the analysis module 36 to obtain an analysis result. Lastly, in step S409, the cloud medical analysis platform 120 sends the analysis result to the electronic device 100.

It should be mentioned here that, in an exemplary embodiment of the invention, the CADe module 36a and the CADx module 36b of the analysis module 36 can respectively be implemented using a self-learning model (such as a deep-learning model, but not limited thereto), and the deep-learning model can be trained via a plurality of training images. In an embodiment, the deep-learning model adopts a multi-resolution convolutional neural network. In general, the deep-learning model includes a plurality of layers, such as a plurality of convolution layers, a plurality of pooling layers, and a plurality of fully-connected layers. During the operation of the plurality of layers, a device having better computing ability is often needed for execution to effectively reduce process time. Therefore, when the computing ability of the cloud medical analysis platform 120 is better than the computing ability of the electronic device 100, the function of the CADe module 36a or the CADx module 36b can be executed by the cloud medical analysis platform 120 using the deep-learning model. Moreover, since the electronic device 100 only sends the feature value to the cloud medical analysis platform 120 for analysis, the electronic device 100 does not need to send a complete medical image to the cloud medical analysis platform 120. As a result, the transmission amount of data can be effectively reduced, and the performance of the system can be increased.

In particular, in an exemplary embodiment, a portion of the layer in the deep-learning model of the analysis module 36 can also be first executed by the electronic device 100. For instance, in step S403, the feature value acquisition module 24b of the electronic device 100 can input the medical image to a portion of the layer in the deep-learning model to obtain the first feature value. After the cloud medical analysis platform 120 obtains the first feature value, the first feature value can be inputted to another portion of the layer in the deep-learning model in step S407 to obtain the analysis result. Via this method, the operational efficiency of the deep-learning module can be increased, and the operation of the system 1000 for cloud medical image analysis can be more flexible.

It should be mentioned that, in the invention, the implementation of the CADe module 36a and the CADx module 36b in the analysis module 36 is not limited, and in another embodiment, the CADe module 36a and the CADx module 36b can also be respectively implemented using a machine-learning algorithm (such as logic regression or support vector machine) based on actual application requirement and be trained via a plurality of training images.

To more clearly describe the operating method of the system 1000 for cloud medical image analysis, a plurality of embodiments is provided hereinafter.

First Embodiment

Referring to all of FIG. 1 to FIG. 3, in the first embodiment of the invention, the electronic device 100 can obtain a medical image via the image input module 24a. Next, the electronic device 100 can obtain a feature value according to the medical image via the method of generating the first feature value. After the feature value is obtained, the electronic device 100 can send the feature value to the cloud medical analysis platform 120 via a wired or wireless method. The cloud medical analysis platform 120 inputs the received feature value to the CADe module 36a in the analysis module 36 to generate an analysis result. In particular, the CADe module 36a is used to determine the location of the tumor in the medical image according to the feature value and generate a corresponding analysis result. In other words, the analysis result generated by the CADe module 36a is used to represent the location of the tumor in the medical image.

Next, the cloud medical analysis platform 120 can send the analysis result to the electronic device 100. The electronic device 100 can display via the human-machine display interface (such as a touch display screen (not shown)) thereof such that the user (such as a doctor) can learn the location of the tumor in the medical image.

However, it should be mentioned that, the electronic device 100 can also send a feedback message to the cloud medical analysis platform 120 according to the analysis result. The cloud medical analysis platform 120 uses the feedback message and the first feature value of the medical image to make the CADe module 36a self-learn. For instance, in the analysis result, misjudgment of tumor location may occur or tumor location may be missing, and the user (such as a doctor) of the electronic device 100 can add a misjudged tumor location and circle out a missing tumor location in the feedback message, and the cloud medical analysis platform 120 can make the CADe module 36a self-learn according to the feedback message.

In other words, in the first embodiment, the electronic device 100 can obtain a feature value. The cloud medical analysis platform 120 executes the CADe module 36a according to the feature value sent by the electronic device 100 and generates an analysis result. The user of the electronic device 100 can learn the location of the tumor in the medical image according to the analysis result and can provide a feedback message to the cloud medical analysis platform 120 to make the CADe module 36a self-learn.

Second Embodiment

Referring to all of FIG. 1 to FIG. 3, in the second embodiment of the invention, the electronic device 100 can obtain a medical image via the image input module 24a. In particular, the medical image in the second embodiment is a medical image of a tumor region. For instance, the electronic device 100 can learn the location of the tumor via the analysis result returned by the first embodiment, and the electronic device 100 can cut the medical image in the first embodiment according to the location of the tumor to capture the medical image of the tumor region as the medical image of the second embodiment.

After the medical image of the second embodiment is obtained, the electronic device 100 can obtain the feature value according to the medical image via the method of generating the first feature value and send the feature value to the cloud medical analysis platform 120. The cloud medical analysis platform 120 inputs the received feature value to the CADx module 36b in the analysis module 36 to generate an analysis result. In particular, the CADx module 36b is used to determine whether the tumor in the medical image is benign or malignant according to the feature value and generate a corresponding analysis result. In other words, the analysis result generated by the CADx module 36b is used to represent whether the tumor in the medical image of the second embodiment is benign or malignant.

Next, the cloud medical analysis platform 120 can send the analysis result to the electronic device 100. The electronic device 100 can display via the human-machine display interface (such as a touch display screen (not shown)) thereof such that the user (such as a doctor) can learn whether the tumor in the medical image is benign or malignant.

However, it should be mentioned that, the electronic device 100 can also send a feedback message to the cloud medical analysis platform 120 according to the analysis result. The cloud medical analysis platform 120 uses the feedback message and the first feature value of the medical image to make the CADx module 36b self-learn. For instance, in the analysis result, a malignant tumor may be misjudged as benign or a benign tumor may be misjudged as malignant. The user (such as a doctor) of the electronic device 100 can add the correct determination result in the feedback message, and the cloud medical analysis platform 120 can make the CADx module 36b self-learn according to the feedback message.

In other words, in the second embodiment, the electronic device 100 can obtain a feature value. The cloud medical analysis platform 120 executes the CADx module 36b according to the feature value sent by the electronic device 100 and generates an analysis result. The user (such as a doctor) of the electronic device 100 can learn whether the tumor in the medical image is benign or malignant according to the analysis result and can provide the feedback message to the cloud medical analysis platform 120 to make the CADx module 36b self-learn.

Third Embodiment

Referring to all of FIG. 1 to FIG. 3, in the third embodiment of the invention, the electronic device 100 can obtain a medical image via the image input module 24a, and the medical image is, for instance, the medical image of the first embodiment. After the medical image is obtained, the electronic device 100 can obtain a feature value according to the medical image via the method of generating the first feature value. After the feature value is obtained, the electronic device 100 can send the feature value to the cloud medical analysis platform 120. The cloud medical analysis platform 120 inputs the received feature value to the CADe module 36a in the analysis module 36 to determine the location of the tumor in the medical image.

For instance, when the CADe module 36a performs an operation using a region-wise algorithm, the CADe module 36a can determine the location of the tumor in the medical image corresponding to the feature value using the feature value obtained from the electronic device 100. When the CADe module 36a performs an operation using a pixel-wise algorithm, the CADe module 36a can determine whether the various pixels in the medical image corresponding to the feature value are a tumor using the feature value obtained from the electronic device 100 and determine the location of the region formed by the pixels of a possible tumor as the location of the tumor.

When the location of the tumor in the medical image is determined, a tumor may be present in the medical image. At this point, the CADe module 36a can generate a second feature value according to the received feature value. In particular, the second feature value is, for instance, the same as the feature value received by the CADe module 36a from the electronic device 100 or a feature value generated from another process, and is not limited thereto.

Next, the CADe module 36a sends the second feature value to the CADx module 36b. The CADx module 36b generates an analysis result according to the second feature value. In particular, the CADx module 36b is used to determine whether the tumor in the medical image is benign or malignant according to the second feature value and generate a corresponding analysis result. In other words, the analysis result generated by the CADx module 36b is used to represent whether the tumor in the medical image is benign or malignant.

Next, the cloud medical analysis platform 120 can send the analysis result to the electronic device 100. The electronic device 100 can display via the human-machine display interface (such as a touch display screen (not shown)) thereof such that the user (such as a doctor) can learn whether the tumor in the medical image is benign or malignant.

Similarly, the electronic device 100 can also send the feedback message to the cloud medical analysis platform 120 according to the analysis result such that the cloud medical analysis platform 120 makes the CADx module 36b self-learn according to the feedback message and the second feature value of the medical image.

In other words, in the third embodiment, the electronic device 100 can obtain a feature value. The cloud medical analysis platform 120 respectively executes the CADe module 36a and the CADx module 36b according to the feature value sent by the electronic device 100 and generates an analysis result. The user (such as a doctor) of the electronic device 100 can learn whether the tumor in the medical image is benign or malignant according to the analysis result and can provide the feedback message to the cloud medical analysis platform 120 to make the CADx module 36b self-learn.

Based on the above, the system and method for cloud medical image analysis of the invention can generate a feature value according to a medical image via an electronic device, and the cloud medical analysis platform executes the function of a CADe module and/or a CADx module according to the feature value and returns the location of the tumor and/or the diagnostic result of the tumor to the electronic device, and the cloud medical analysis platform can even have a self-learning mechanism based on the feedback from the electronic device to optimize the cloud medical analysis platform. Via this method, the electronic device does not need to actually execute the CADe module and/or the CADx module, and therefore the computational load of the electronic device can be effectively reduced. Moreover, since the electronic device only needs to send the feature value to the cloud medical analysis platform for analysis, the electronic device does not need to send a complete medical image to the cloud medical analysis platform. As a result, the transmission amount of data can be effectively reduced, and the response time of the system can be reduced.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A system for cloud medical image analysis, comprising:
    a cloud medical analysis platform, including a first processor and a first communication device; and
    an electronic device, including a second processor and a second communication device, wherein
    in the electronic device, the second processor obtains a medical image, inputs the medical image to a portion of layers in an analysis module to obtain a first feature value, and sends the first feature value to the cloud medical analysis platform by the second communication device,
    in the cloud medical analysis platform, the first processor receives the first feature value by the first communication device, inputs the first feature value to another portion of the layers in the analysis module to obtain an analysis result, and sends the analysis result to the electronic device by the first communication device.

2. The system for cloud medical image analysis of claim 1, wherein:
    the analysis module comprises a deep-learning model.

3. The system for cloud medical image analysis of claim 1, wherein the analysis module comprises a deep-learning model, and the deep-learning model adopts a multi-resolution convolutional neural network.

4. The system for cloud medical image analysis of claim 1, wherein the analysis module comprises a self-learning model.

5. The system for cloud medical image analysis of claim 1, wherein the analysis module comprises a computer-aided detection (CADe) module,
    wherein the first processor executes the CADe module to determine a location of a tumor, and the analysis result is used to represent the location of the tumor in the medical image.

6. The system for cloud medical image analysis of claim 1, wherein the analysis module comprises a computer-aided diagnosis (CADx) module,
    wherein the first processor executes the CADx module to provide a diagnostic suggestion, and the analysis result is used to represent the diagnostic suggestion in the medical image.

7. The system for cloud medical image analysis of claim 1, wherein the analysis module comprises a CADe module and a CADx module,
    the first processor executes the CADe module to obtain a second feature value according to the first feature value,
    the first processor executes the CADx module to generate the analysis result according to the second feature value, wherein the analysis result is used to represent a diagnostic suggestion in the medical image.

8. The system for cloud medical image analysis of claim 1, wherein
    the electronic device sends a feedback message to the cloud medical analysis platform according to the analysis result,
    the cloud medical analysis platform uses the feedback message and the first feature value of the medical image to make the analysis module self-learn.

9. A method for cloud medical image analysis for a system for cloud medical image analysis having a cloud medical analysis platform and an electronic device, wherein the cloud medical analysis platform includes a first processor and a first communication device, and the electronic device includes a second processor and a second communication device, and the method comprises:
    obtaining, by the second processor, a medical image in the electronic device;
    inputting, by the second processor, the medical image to a portion of layers in an analysis module in the electronic device to obtain a first feature value;
    sending, by the second communication device, the first feature value to the cloud medical analysis platform in the electronic device;
    inputting, by the first processor, the first feature value to another portion of the layers in the analysis module in the cloud medical analysis platform to obtain an analysis result; and
    sending, by the first communication device, the analysis result to the electronic device in the cloud medical analysis platform.

10. The method for cloud medical image analysis of claim 9, wherein:
    the analysis module comprises a deep-learning model.

11. The method for cloud medical image analysis of claim 9, wherein the analysis module comprises a deep-learning model, and the deep-learning model adopts a multi-resolution convolutional neural network.

12. The system for cloud medical image analysis of claim 9, wherein the analysis module comprises a self-learning model.

13. The method for cloud medical image analysis of claim 9, wherein the analysis module comprises a CADe module, wherein the analysis result is used to represent a location of a tumor in the medical image, and the location of the tumor is determined by the CADe module executed by the first processor.

14. The method for cloud medical image analysis of claim 9, wherein the analysis module comprises a CADx module, wherein the analysis result is used to represent a diagnostic suggestion in the medical image, and the diagnostic suggestion is determined by the CADx module executed by the first processor.

15. The method for cloud medical image analysis of claim 9, wherein the analysis module comprises a CADe module and a CADx module, and the method further comprises:
    obtaining a second feature value via the CADe module executed by the first processor according to the first feature value; and
    generating the analysis result via the CADx module executed by the first processor according to the second feature value, wherein the analysis result is used to represent a diagnostic suggestion in the medical image.

16. The method for cloud medical image analysis of claim 9, further comprising:
    sending a feedback message to the cloud medical analysis platform via the electronic device according to the analysis result; and using the feedback message and the first feature value of the medical image to make the analysis module self-learn via the cloud medical analysis platform.

* * * * *